United States Patent [19]

Tricerri Zumin et al.

[11] 4,181,740
[45] Jan. 1, 1980

[54] INDOLYL ACETIC ACID DERIVATIVE

[75] Inventors: Silvia Tricerri Zumin, Carimate; Alberto Bianchetti, Milan, both of Italy

[73] Assignee: Pierrel S.p.A., Italy

[21] Appl. No.: 796,607

[22] Filed: May 13, 1977

[30] Foreign Application Priority Data

May 19, 1976 [GB] United Kingdom ............... 20596/76

[51] Int. Cl.$^2$ ................... A61K 31/405; C07D 209/04
[52] U.S. Cl. ........................... 424/274; 260/326.13 A; 260/326.13 B; 260/326.14 A; 544/109; 544/327; 536/18; 546/201; 546/347; 548/344

[58] Field of Search ............. 260/326.13 A, 326.14 A, 260/326.13 B; 424/274; 544/109, 327; 536/18; 546/201, 347; 548/344

[56] References Cited

U.S. PATENT DOCUMENTS

| 3,669,987 | 6/1972 | Sato et al. | 260/326.13 A |
| 3,910,952 | 10/1975 | Boltze et al. | 260/326.13 A |

Primary Examiner—Jose Tovar
Attorney, Agent, or Firm—Bacon & Thomas

[57] ABSTRACT

The present invention provides 1-(p-azidobenzoyl)-5-methoxy-2-methyl-3-indolylacetic acid and its pharmaceutically acceptable salts and esters and processes of preparation.

9 Claims, No Drawings

INDOLYL ACETIC ACID DERIVATIVE

This invention relates to 1-aroyl-3-indolylacetic acid compounds.

1-aroyl and heteroaroyl-3-indolyl-lower aliphatic acid compounds are known and have a high degree of anti-inflammatory activity and are effective in the prevention and inhibition of granuloma tissue formation. Certain of these compounds are of value in the treatment of arthritic and dermatological disorders and similar conditions which are responsive to treatment with anti-inflammatory agents. One of the most active compounds is known under the trade name Indomethacin, which is 1-p-chlorobenzoyl-5-methoxy-2-methyl-3-indolyl-acetic acid.

The present invention provides 1-(p-azidobenzoyl)-5-methoxy-2-methyl-3-indolylacetic acid i.e. a compound of the formula:

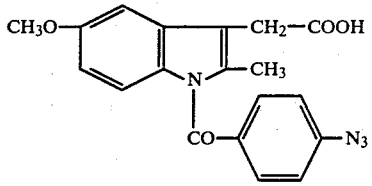

and its pharmaceutically acceptable salts and esters.

It has been found that the presence of the azido substituent in the benzoyl group gives the compound a pharmacological activity similar to that of Indomethacin but with, surprisingly, much lower toxicity and degree of undesirable side effects.

The compound itself is a yellow crystalline powder having a melting point of 170°–172° C. (dec.). The crystals are soluble in dimethylformamide and dimethylsulfoxide, slightly soluble in methanol and ethanol and practically insoluble in water.

The present invention also provides processes for the synthesis of the above described compounds. p One convenient method for preparation is from the corresponding p-amino compound. This compound is described in British Pat. No. 1,159,626 and may be synthesized by standard procedures as, for example, by acylating sodium p-methoxy-phenylhydrazine sulfonate with p-nitrobenzoylchloride to the asymmetrical N' -(p-nitrobenzoyl)-p-methoxy-phenylhydrazine. 1-(p-Aminobenzoyl)-5-methoxy-2-methyl-3-indolyacetic acid is obtained in two steps by Fischer indole condensation with levulinic acid and subsequent reduction of the p-nitro group. The p-azido group is introduced by diazotization followed by treatment with hydrazoic acid.

Alternatively, an indolylacetic acid ester of formula II

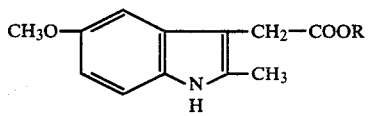

wherein R is a lower alkyl, an aralkyl or a vinyl-like group, can be prepared, for example by esterifying the known free acid with alcohols, by direct synthesis from the desired ester of the levulinic acid in the original synthesis of the indole ring, or by transesterification of other esters.

The acylation of the indole nitrogen is preferably conducted by treating a compound of formula II with an alkali metal hydride to form a metal salt and then intimately contacting it with a p-azidobenzoyl or a p-nitrobenzoyl halide in an anhydrous solvent medium. The ester group can then be removed in a number of ways.

The anti-inflammatory activity of the free acid compound of the present invention was evaluated in rats by the cotton pellets induced granuloma test (Meier R., Schuler W. and Desaulles—Experientia 1950, 6, 469), administering the compound orally each day for 7 days.

The antiedema activity of this compound was evaluated by administering it acutely before the injection of carragenin into the plantar surface of rat paw and measuring the inhibition (Winter C. A., Risley E. A. and Nuss G. W.—J. Pharmacol. Exp. Ther., 1963, 141, 369) of the edema volume.

The compound antagonizes granuloma and edema formation at a dose of 3 mg/kg b.w. orally (approximate inhibition of 29% and 46% respectively). In the granuloma test, the compound was slightly less active than Indomethacin, but it was as active as Indomethacin in inhibiting the edema formation.

The analgesic activity was evaluated in mice by measuring the percentage of animals protected from writhing induced by phenylquinone intraperitoneal injection (Henders L. C., Forsaith J.—J. Pharmacol. Exp. Ther., 1959, 125, 237). The oral $ED_{50}$ (dose preventing writhing in 50% of mice) was about 2.5 mg/kg b.w., whereas that of Indomethacin was 1.25 mg/kg b.w.

The $LD_{50}$ values after acute oral administration of the compound in male mice and rats were 250 mg/kg b.w. and 85 mg/kg b.w. respectively, while the corresponding $LD_{50}$ values for Indomethacin were 13.5 mg/kg b.w. and 10 mg/kg b.w.; the $LD_{50}$ values in female mice and rats were respectively 240 mg/kg b.w. and 105 mg/kg b.w. for the invention compound and 23 mg/kg b.w. and 17 mg/kg b.w. for Indomethacin. When administered orally to rats at several dose levels the compound turned out to be about 10 times less ulcerogenic than Indomethacin.

Accordingly, the present invention provides therapeutic compositions comprising the compound of the invention, or a pharmaceutically acceptable salt or ester thereof, as an active ingredient, together with a conventional pharmaceutically acceptable carrier, in the form of tablets, capsules, ampoules or suppositories with a dosage ranging from 25 to 150 mg/dosage unit.

Any pharmaceutically acceptable inorganic or organic salt or ester may be used. Such salts are those formed with a metal of Group I, II, III of Mendeleev's periodic table e.g., sodium, potassium, magnesium, calcium, and the like. Organic salts include amine salts such as those salts formed with ethanolamine, triethanolamine, ethylendiamine, morpholine, histidine, arginine, lysine, glucosamine, piperidine, thiamine, pyridoxamine and the like. Any conventional pharmaceutically acceptable esters may be used, preferably lower alkyl as already described with respect to the process and in particular $C_{1-4}$ lower alkyl. It is clear that mixtures of the above are also contemplated.

As indicated, the compositions may be administered by the oral, parenteral or rectal routes. The compositions may thus be solid or liquid and may take the usual forms of tablets, coated tablets, capsules, solutions, syrups, suppositories and parenteral preparations such as injection ampoules. The carriers and excipients used may include the conventional ingredients, for example, talc, gum arabic, lactose, starch, magnesium stearate, cocoa butter, sterile aqueous or non-aqueous vehicles, animal or vegetable fatty substances, paraffin derivatives, glycols, wetting, dispersing and emulsifying agents and preservatives. The following Examples illustrate the invention:

EXAMPLE 1

Preparation of 1-(p-azidobenzoyl)-5-methoxy-2-methyl-3-indlylacetic acid.

METHOD A

A hot solution of 5.2 g (15.4 mmol) of 1-(p-aminobenzoyl)-5-methoxy-2-methyl-3-indolylacetic acid in 65 ml of acetic acid is rapidly cooled to 25°–30° C., taking care to avoid crystallization.

This cold solution and a solution of 1.145 g (16.6 mmol) of sodium nitrite in 40 ml of water are added simultaneously to 18 ml of concentrated hydrochloric acid at −5° C. with stirring.

The resulting solution (~25° C.) is red coloured and on cooling to 0° C. a crystalline solid begins to separate. After 10 minutes a 0° C., an ice-cold solution of 1.057 g (16.25 mmol) of sodium azide in 40 ml of water is added in portions.

A cream coloured pecipitate forms immediately, accompanied by copious evolution of nitrogen. The reaction is completed when no more red colour is visible. If necessary, a further little excess of $NaN_3$ solution may be added.

Stirring is continued for 10 minutes at 0° C. and then the mixture is extracted with ethylacetate.

The organic phase is separated, washed with water, dried over $Na_2SO_4$ and concentrated in vacuo to give 5.67 g (100%) of 1-(p-azidobenzoyl)-5-methoxy-2-methyl-3-indolylacetic acid.

Thin layer chromatography on silica gel gives one spot in the system chloroform-ethanol 95:5.

An analytical sample is obtained by crystallization from methanol-water: Mp. 170°–172° C. with gas evolution;

IR (KBr) doublet at 4.69–4.76$\mu$ ($N_3$), 5.85$\mu$ (acid C=O), 5.97$\mu$ (amide C=O).

METHOD B

A mixture of 950 g (2.808 mol.) of 1-(p-aminobenzoyl)-5-methoxy-2-methyl-3-indolylacetic acid in 10 l. water is brought to pH 8 with NaOH 2.5 N and stirred until dissolution of the solid. To this solution 240 g (3.48 mol.) of sodium nitrite m 3 l. water are added, then the solution is poured slowly, over a 2.5 hours period, into an ice-cold well stirred mixture of 25 l. of ethylacetate and 3.2 l. of concentrated hydrochloric acid. A copious red coloured precipitate is formed. After 20 minutes at 0° C., 250 g (3.85 mol.) of sodium azide are added under stirring, in portions, over 60 minutes.

Solid dissolution is a-companied by evolution of nitrogen. The reaction is complete when no more red colour is visible. The organic phase is separated, washed with 120 l. water, dried over $Na_2SO_4$, filtered with Celite (Registered Trade Mark) and concentrated in vacuo up to 7–8 l. A total of 40 l. petrol ether is added to the slurry. The mixture is stirred for two hours at room temperature, the solid is filtered, washed with petrol ether and dried in vacuo at 40° C. The crude powder is the nearly pure desired product (yielded 921 g, 90%). Another quantity (30 g) may be recovered from the filtrate after concentration.

EXAMPLE 2

Preparation of methyl 1-(p-nitrobenzoyl)-5-methoxy-2-methyl-3-indolylacetate.

To a solution of 23.3 g (0.1 mole) of methyl-5-methoxy-2-methyl-3-indolylacetate in 50 ml of dry toluene are added 3 g of 80% sodium hydride. The mixture is stirred at room temperature for 4 hours and then a solution of 18.56 g (0.1 mole) of p-nitrobenzoylchloride in 80 ml of dry toluene is added slowly thereto over a 30-minute period.

The reaction mixture is boiled for 30 hours. After cooling it is poured into 400 ml of ice-water and 15 ml of acetic acid.

The separated toluene solution is washed with a large quantity of water, dried over sodium sulfate and evaporated to a syrup which is dissolved in ether.

Slow evaporation of this solution in an open beaker gives 10 g of methyl-1-(p-nitrobenzoyl)-5-methoxy-2-methyl-3-indolylacetate as yellow prisms.

Another quantity may be recovered from the oily residue after chromatography on a silica gel column (elution with benzene).

Mp 134°–135° C. (cryst, from MeOH).

EXAMPLE 3

Preparation of methyl-1-(p-azidobenzoyl)-5-methoxy-2-methyl-3-indolylacetate.

The title compound is prepared by condensing 18.16 g (0.1 mole) of p-azidobenzoyl chloride with 0.1 mole of methyl-5-methoxy-2-methyl-3-indolylacetate following the procedure described in Example 2.

The reaction mixture is stirred under nitrogen for 48 hours at 50°–60° C. The product is isolated as described in Example 2 to give substantially pure, yellow coloured methyl-1-(p-azidobenzoyl)-5-methoxy-2-methyl-3-indolylacetate.

The infrared spectrum shows no N—H absorption near the 2.9–3.0$\mu$ region but a strong doublet at 4.7–4.75$\mu$ indicates an azido group and strong C=P absorptions at 5.75 and 5.98$\mu$ are characteristic for ester and amide functional groups respectively. cl EXAMPLE 4

Preparation of 1-(p-nitrobenzoyl)-5-methoxy-2-methyl-3-indolylacetic acid.

A solution of 4.9 g (12.8 mmol) of methyl-1-(p-nitrobenzoyl)-5-methoxy-2-methyl-3-indolylacetate in 40 ml of acetic acid containing 400 mg of p-toluene-sulfonic acid is refluxed for 20 hours and then concentrated in vacuo. p The gummy residue is extracted with ethyl acetate.

The extract is filtered from insoluble material, washed with water and dried over sodium sulfate.

Removal of the solvent under reduced pressure affords the desired product as yellow crystals, mp 185°–186° C. (cryst. from EtOH).

EXAMPLE 5

Preparation of 1-(p-aminobenzoyl)-5-methoxy-2-methyl-3-indolylacetic acid.

METHOD A 20 g (54.3 mmol) of 1-(p-nitrobenzoyl)-5-methoxy-2-methyl-3-indolylacetic acid is dissolved in 1200 ml of hot methanol and hydrogenated in the presence of 2.64 g of 10% palladium on charcoal as catalyst. After 164 mmol of hydrogen have been consumed, the hydrogenation is stopped, and the solution filtered to remove the catalyst.

The filtrate is concentrated in vacuo to give, in nearly theoretical yield, the p-amino derivative.

A crystallization from methanol-water gave an analytical sample: mp 198°–200° C. (dec.) crystals from MeOH—H$_2$O.

METHOD B

A mixture of 2.36 kg (6.4 mol.) of 1-(p-nitrobenzoyl)-5-methoxy-2-methyl-3-indolylacetic acid and 236 g of 10% palladium charcoal in 23.6 l. water and 28 l. methanol is sitrred, cooled and maintained at about 15° C. To this mixture 1.1 l. of hydrazine hydrate 100% (22.6 mol.) in 3 l. water is slowly added, over a 60 minute period. Then it is stirred for one hour allowing the temperature to rise to 30° C. and then for 3.5 hours at this temperature.

The catalyst is removed by filtration and the pH of the solution is corrected from 8 to 2 with 15% hydrochloric acid (~3.2 l. HCl 15%). The mixture is stirred for two hours at room temperature. The precipitate is filtered, washed with water just to pH 5 (25 l.) and dried. The white solid weights 1.955 kg (90.2%) and is substantially pure 1-(p-aminobenzoyl)-5-methoxy-2-methyl-3-indolylacetic acid.

What we claim is:

1. The compound 1-(p-azidobenzoyl)-5-methoxy-2-methyl-3-indolylacetic acid or pharmaceutically acceptable salts or C$_1$-C$_4$ lower alkyl esters thereof.

2. A therapeutic composition comprising the compound of claim 1, or a salt or ester thereof, as an active ingredient, together with a pharmaceutically acceptable carrier.

3. A therapeutically active pharmaceutical composition of claim 2, in which the dosage of the active ingredient is from 25 to 150 mg/dosage unit.

4. The compound of claim 1 which is the acid.

5. The compound of claim 1 wherein the pharmaceutically acceptable salt is the sodium, potassium, magnesium or calcium salt.

6. The compound of claim 1 wherein the pharmaceutically acceptable salt is an amine salt formed with ethanolamine, triethanolamine, ethylenediamine, morpholine, histidine, arginine, lysine, glucosamine, piperidine, thiamine, or pyridoxamine.

7. The compound of claim 1 wherein the pharmaceutically acceptable ester is a C$_{1-4}$ lower alkyl ester.

8. The compound of claim 10 which is methyl-1-(p-azidobenzoyl)-5-methoxy-2-methyl-3-indolylacetate.

9. A therapeutic composition of claim 2 in the form of tablets, capsules, suppositories or ampoules.

* * * * *

UNITED STATES PATENT AND TRADEMARK OFFICE
CERTIFICATE OF CORRECTION

PATENT NO. : 4,181,740
DATED : January 1, 1980
INVENTOR(S) : Tricerri Zumin et al It is certified that error appears in the above—identified patent and that said Letters Patent is hereby corrected as shown below:

Claim 8 should read as follows:

8. The compound of claim 1 which is methyl-1-(p-azidobenzoyl)-5-methoxy-2-methyl-3-indolylacetate.

Signed and Sealed this

Eighth Day of July 1980

[SEAL]

Attest:

Attesting Officer

SIDNEY A. DIAMOND

Commissioner of Patents and Trademarks